United States Patent [19]

Ruthrof et al.

[11] Patent Number: 4,656,870
[45] Date of Patent: Apr. 14, 1987

[54] ULTRASONIC TESTING DEVICE

[75] Inventors: Klaus Ruthrof, Erlangen; Georg Hölzler, Möhrendorf; Rudolf Körner, Leinburg, all of Fed. Rep. of Germany

[73] Assignee: Kraftwerk Union Aktiengesellschaft, Mülheim/Ruhr, Fed. Rep. of Germany

[21] Appl. No.: 759,125

[22] Filed: Jul. 25, 1985

[30] Foreign Application Priority Data

Jul. 30, 1984 [DE] Fed. Rep. of Germany ....... 3428056

[51] Int. Cl.$^4$ ............................................. G01N 29/04
[52] U.S. Cl. ......................................... 73/629; 73/632
[58] Field of Search ................... 73/629, 632, DIG. 1

[56] References Cited

U.S. PATENT DOCUMENTS

| | | | |
|---|---|---|---|
| 3,485,088 | 12/1969 | O'Connor | 73/629 |
| 3,821,834 | 7/1974 | McElroy | 73/632 |
| 4,365,515 | 12/1982 | Abts | 73/632 |

*Primary Examiner*—Anthony V. Ciarlante
*Attorney, Agent, or Firm*—Herbert L. Lerner; Laurence A. Greenberg

[57] ABSTRACT

Ultrasonic testing device with a test head which includes an electromechanical transducer, especially a piezoelectric oscillator, with an ultrasonic equipment and with a shielded cable which connects the test head to the ultrasonic equipment. The test head has two electrically conducting shields which surround the transducer in cup-fashion. The two shields are connected to the outer conductors of the triple coaxial cable. The outer conductor of the cable is connected to a metal housing of the ultrasonic equipment and is grounded.

10 Claims, 2 Drawing Figures

ULTRASONIC TESTING DEVICE

BACKGROUND OF THE INVENTION

Field of the Invention

The invention relates to an ultrasonic testing device with a test head which comprises an electromechanical transducer, particularly a piezoelectric oscillator, with an ultrasonic equipment and a shielded cable which connects the test head to the ultrasonic equipment.

SUMMARY OF THE INVENTION

It is an object of the invention to reduce the interference proneness of the above-mentioned testing device which leads, in spite of the shielded cable, to signals which are in error due to electric and/or electromagnetic interference fields. Such interference fields can be caused by relatively weak extraneous high-frequency radiations, for instance by radio broadcasting, but can also be caused by electric arc welding equipment, etc. The interference is picked up here inductively and/or capacitively or metallically and falsifies the ultrasonic measuring signal.

With the foregoing and other objects in view, there is provided in accordance with the invention an ultrasonic testing device with a test head which comprises an electromechanical transducer, especially a piezoelectric oscillator, with an ultrasonic equipment and with a shielded cable which connects the test head to the ultrasonic equipment the combination therewith of: two electrically conducting shields which surround the transducer in cup-fashion; a triple coaxial cable connecting the test head to the ultrasonic equipment; the two shields connected to the outer conductors of the triple coaxial cable; and at least the outer conductor of the cable is connected to a metal housing of the ultrasonic equipment and is grounded.

Other features which are considered as characteristic for the invention are set forth in the appended claims.

Although the invention is illustrated and described herein as embodied in an ultrasonic testing device, it is nevertheless not intended to be limited to the details shown, since various modifications may be made therein without departing from the spirit of the invention and within the scope and range of equivalents of the claims.

BRIEF DESCRIPTION OF THE DRAWINGS

The invention, however, together with additional objects and advantages thereof will be best understood from the following description when read in connection with the accompanying drawings, in which.

DESCRIPTION OF THE PREFERRED EMBODIMENTS

According to the invention the test head has two electrically conducting shields which surround the transducer in cup-fashion. The two shields are connected to the outer conductors of the triple coaxial cable, and at least the outermost conductor of the cable is connected to a metal housing of the ultrasonic equipment and is grounded.

By virtue of the invention, far-reaching decoupling of the testing device from external interference fields is achieved. This is amazing for the reasons that first, it was believed that enough had been done in this respect with a shielded cable and secondly, because the further shielding according to the invention permits proper measurements and tests under circumstances which heretofore had been considered hopeless.

Advantageously, electrically conducting foils or plastic coated with conducting material can serve as shields of the test head. Optionally, such shields by thermoplastic deformation or by cold working, can be applied so tightly to insulating material parts of the testing head that a firm hold is produced. However, the shielding can also be cemented on. In any case, it is advantageous if the cable is connected to the shields of the test head and to the metal housing of the ultrasonic equipment via plug-in contacts because this facilitates the assembly and disassembly of the testing device. In addition, measurements of the electrical characteristics of the test head and the cable can be performed, for instance, for adjustment purposes by means of the plug contacts.

An embodiment of the testing device according to the invention which has proven itself particularly well in trials, comprises rigid metal cups serving as shields of the test head. Further details of the invention can be seen from the following description of embodiment examples, referring to the attached drawings.

Figure 1:
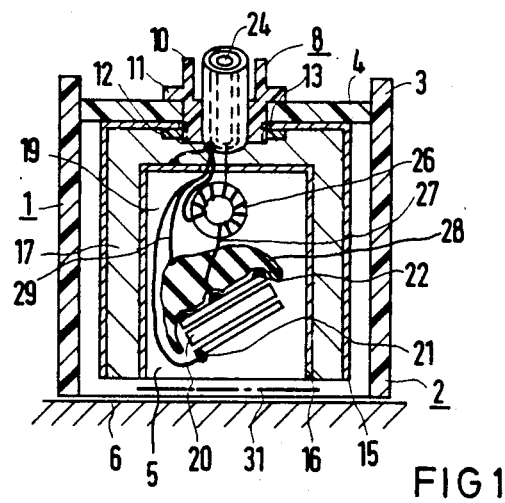
FIG. 1 diagrammatically illustrates a test head of an ultrasonic testing device, in section, in accordance with the invention, in which are shown two spaced concentric, cup-shaped shields surrounding a piezoelectric oscillator.

FIG. 1 shows the mechanical design of a "triaxial" design of an ultrasonic test head 1, which can be used in a nuclear power station for sensitive measurements even though, because of short shutdown times, heavy-current electric arc welding equipment and radio voice equipment are operated in the immediate vicinity. The test head 1 has an insulating-material housing 2 which is composed of a cylindrical jacket 3 and a flat bottom 4 to form a cup open on one side. The opening 5 of the cup provided for the sound output faces the surface of the power station component 6 to be tested, for instance, a pressure-carrying pipeline.

A triaxial jack 8 for connecting a triaxial cable (FIG. 2) is mounted in the center of the bottom 4. The jack 8 comprises a rotation-symmetrical insulating-material body 10 which is clamped to the bottom 4 by a shoulder 11 and a fastening nut 12. The jack 8 is screwed to a threaded connector stub 13 of the insulating material body 10. Plug contacts 14 are mounted in the insulating-material body.

A first cup-shaped shield which is in the form of a rigid stiff metal cup 15, which is for instance, deep drawn of aluminum or copper sheet and is arranged concentrically to the housing 2, can be fastened by the fastening nut 12. This first shield 15 surrounds a second cup-shaped shield 16 which is again arranged concentrically and can likewise be shaped as a metal cup. The annular space 17 between the shields 15 and 16 has a thickness equal to about ¼ to 1/10 of the diameter of the smaller cup. Space 17 can be filled with an insulating plastic, preferably a rubber-elastic foam material which makes possible a detachable locking of the shields 15, 16 and also assures a high-resistance insulation ($>20$ M$\Omega$).

In the interior 19 of the shield 16, there is a piezoelectric oscillator 20 with an electrode 21 on one side and an electrode 22 on the other side of the oscillator. Contrary to conventional designs, the electrode 22 facing the interior of the cup is connected to the central conductor 24 of the triaxial jack 8. The electrode 21, facing the test piece 6, on the other hand is connected to the shield 16 and is tied, together with the latter, to the chassis and/or is grounded. This reduces particularly the capacitive pick-up of interference fields substantially.

In the embodiment example according to FIG. 1, the "hot" electrode 22 is connected via a cup or ring-core transformer 26 for matching to cable 9 to the central conductor 24 which is likewise located, shielded, in the interior of the cup 19. To reduce inductive pick-up, magnetic shields of the transformer 26 can be provided, for instance, the cup 16 can be made of ferromagnetic material.

An electrically conducting damping mass 28 which consists, for instance, of kneadable plastic with conductive particles, for instance graphite or metal powder, is further provided in the interior 19, in the vicinity of the oscillator 20 and the connecting lead 27 leading to the electrode 22. The damping mass 28 can be brought to the potential of the shield 16 by a connecting lead 29 if no satisfactory connection is provided otherwise. Above all, however, the damping mass 28 can replace the shield 16 if its conductivity is high enough and its shape suitably encloses the oscillator 20 in cup-fashion. The electrode 22 and the connecting lead 27 then support sufficient electrical insulation.

To complete the shielding against interference fields in the vicinity of the ultrasonic testing device, the test head 1 can be terminated at the opening 5, provided for the output of the sound, of the cup-shaped shields 15, 16, by an electrically conducting accoustic λ/4 layer 31 which consists of ferromagnetic material, for instance, in the form of a metal foil. The thickness of the layer 31 can also correspond to an uneven multiple of λ/4 order to obtain an effective electrical and/or electromagnetic shield. Similar effects can also be obtained with smaller layer thicknesses than λ/4, for instance, by vapor-depositing electrically conducting materials. The shield 31 can extend over the two shielding cups 15 and 16, as indicated in FIG. 2.

The cable 9 connected to the triaxial jack 8 has a center conductor 33 and two shielding conductors 34 and 35 which surround the former concentrically with the necessary insulation spacing. These three conductors are connected via the plug-in contacts 14 to the electrode 22, to the electrode 21 and the shield 16 and to the shield 15.

Figure 2:
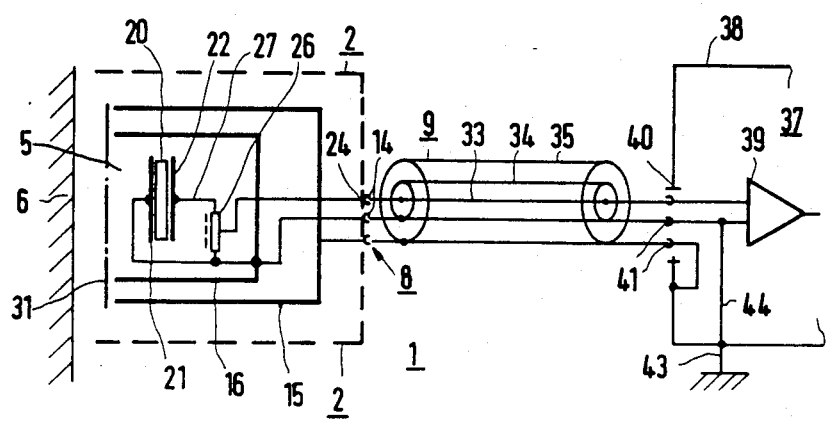
FIG. 2 is a schematic diagram showing the connection of the test head to an ultrasonic equipment.

The other end of the cable 9 leads to an ultrasonic equipment 37, of which only the metal housing 38 and an input amplifier 39 are indicated in FIG. 2. A triaxial plug 40 with plug contacts 41 for connecting the cable 9 to the ultrasonic equipment 37 is mounted in the housing. The conductor 35 leads to the metal housing 38 and via the latter, to the grounding point 43. The inner shielding conductor 34 is connected to the amplifier 39 and is grounded via the line 44. The central conductor 33 likewise leads to the amplifier 39.

The foregoing is a description corresponding, in substance, to German application No. P 34 28 056.1, dated July 30, 1984, international priority of which is being claimed for the instant application and which is hereby made part of this application. Any material discrepancies between the foregoing specification and the specification of the aforementioned corresponding German application are to be resolved in favor of the latter.

There is claimed:

1. Ultrasonic testing device with a test head which comprises, an electromechanical transducer, especially a piezo electric oscillator, and an electrically conducting shield and an insulating housing, with an ultrasonic device and with a shielded cable which connects the test head with the ultrasonic device, the combination therewith of: an additional electrically conducting shield with the two electrically conducting shields spaced from one another arranged to enclose the test head in a cup-fashion; the shielded cable is a triple coaxial cable; the two shields are each separately connected to one of a middle conductor and an outer conductor of the triple coaxial cable; a metal housing around the ultrasonic device, and at least the outer conductor of said cable is connected and grounded to the metal housing of the ultrasonic device.

2. Ultrasonic testing device according to claim 1, wherein the cable is connected to the shields of the test head and the metal housing of the ultrasonic equipment via plug contacts.

3. Ultrasonic testing device according to claim 1, wherein the shields of the test head are formed of electrically conducting foils or conductively coated plastics.

4. Ultrasonic testing device according to claim 1, wherein the shields of the test head are rigid.

5. Ultrasonic testing device according to claim 1, wherein the transducer is disposed with its oscillator side facing away from the bottom of the cups formed by the shields and the oscillator side is connected to the inner shield, and the other side of the transducer facing the bottom of the cup formed by the shields is connected to the center conductor of the cable.

6. Ultrasonic testing device according to claim 1, wherein the transducer is disposed with its oscillator side facing away from the bottom of the cups formed by the shields and the oscillator side is grounded, and the other side of the transducer facing the bottom of the cup formed by the shields is connected to the center conductor of the cable.

7. Ultrasonic testing device according to claim 1, wherein the open side of the cup-shaped shield which is the sound output opening is shielded by a thin electrically conducting layer.

8. Ultrasonic testing device according to claim 7, wherein said electrically conducting layer is vapor-deposited.

9. Ultrasonic testing device according to claim 7, wherein said electrically conducting layer is an accoustical λ/4 layer.

10. Ultrasonic testing device according to claim 1, wherein the shields enclose a cup- or ring-core transformer which is located between the oscillator and the cable.

* * * * *